United States Patent
Rodefeld

(10) Patent No.: US 9,827,357 B2
(45) Date of Patent: Nov. 28, 2017

(54) CAVOPULMONARY VISCOUS IMPELLER ASSIST DEVICE AND METHOD

(71) Applicant: Indiana University Research and Technology Corporation, Indianapolis, IN (US)

(72) Inventor: Mark D. Rodefeld, Zionsville, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 287 days.

(21) Appl. No.: 14/362,452

(22) PCT Filed: Dec. 3, 2012

(86) PCT No.: PCT/US2012/067648
§ 371 (c)(1),
(2) Date: Jun. 3, 2014

(87) PCT Pub. No.: WO2013/082621
PCT Pub. Date: Jun. 6, 2013

(65) Prior Publication Data
US 2014/0336446 A1 Nov. 13, 2014

Related U.S. Application Data

(60) Provisional application No. 61/566,616, filed on Dec. 3, 2011, provisional application No. 61/611,647, filed on Mar. 16, 2012.

(51) Int. Cl.
*A61M 1/10* (2006.01)
*A61M 1/12* (2006.01)

(52) U.S. Cl.
CPC .......... *A61M 1/1036* (2014.02); *A61M 1/101* (2013.01); *A61M 1/1015* (2014.02);
(Continued)

(58) Field of Classification Search
CPC ..... A61N 1/362; A61N 1/3787; A61M 1/101; A61M 1/122; A61M 1/1015; A61M 1/1017; A61M 1/1031
See application file for complete search history.

(56) References Cited

U.S. PATENT DOCUMENTS

| 1,061,142 A | 5/1913 | Tesla |
| 4,957,504 A | 9/1990 | Chardack |

(Continued)

FOREIGN PATENT DOCUMENTS

| EP | 1495773 | 1/2005 |
| EP | 2051751 | 4/2010 |

(Continued)

OTHER PUBLICATIONS

US 8,251,886, 08/2012, Lu et al. (withdrawn)
(Continued)

*Primary Examiner* — Michael Carey
*Assistant Examiner* — Natasha Patel
(74) *Attorney, Agent, or Firm* — John V. Daniluck; Bingham Greenebaum Doll LLP

(57) ABSTRACT

A bearingless and sealless rotary blood pump is disclosed which provides multidirectional flow intended to provide low-pressure, high-volume right-sided partial assist circulatory support in a univentricular Fontan circulation on a permanent basis. The pump includes a housing and an impeller suspended in the center of the housing. The housing incorporates flow optimization features between inlet and outlet ends, as well as with the impeller surface. Large fluid gaps maintained between impeller and housing eliminate any potential for blood flow obstruction. The impeller contains some motor components. It includes a central stator and surrounding rotor. The motor includes a brushless DC outrunner electrical motor design. An electromagnetic stator (Continued)

core is surrounded by a circumferential passive magnetic ring. The rotor is further levitated about the stator spindle by a plurality of axially and radially located passive magnetic and hydrodynamic journal bearings on both ends of the spindle. The rotor is bearingless and sealless. During impeller rotation, blood entering the space between the rotor and stator is induced to flow by centrifugal pumping action and the fluid film separates the stator hydrodynamic bearings from the rotor so that there is no direct mechanical contact between the rotor and stator.

40 Claims, 12 Drawing Sheets

(52) U.S. Cl.
CPC ........ *A61M 1/1017* (2014.02); *A61M 1/1029* (2014.02); *A61M 1/1031* (2014.02); *A61M 1/1086* (2013.01); *A61M 1/122* (2014.02); *A61M 1/125* (2014.02); *A61M 1/127* (2013.01)

(56) References Cited

U.S. PATENT DOCUMENTS

| | | | |
|---|---|---|---|
| 5,049,134 | A | 9/1991 | Golding |
| 5,211,546 | A * | 5/1993 | Isaacson ............... A61M 1/101 415/900 |
| 5,749,855 | A | 5/1998 | Reitan |
| 5,924,848 | A | 7/1999 | Izraelev |
| 6,015,272 | A | 1/2000 | Antaki et al. |
| 6,149,683 | A | 11/2000 | Lancisi et al. |
| 7,476,077 | B2 | 1/2009 | Woodard et al. |
| 7,699,588 | B2 | 4/2010 | Mendler |
| 7,704,054 | B2 | 4/2010 | Horvath et al. |
| 7,798,952 | B2 | 9/2010 | Tansley et al. |
| 7,802,966 | B2 | 9/2010 | Wampler et al. |
| 7,972,122 | B2 | 7/2011 | LaRose et al. |
| 7,997,854 | B2 | 8/2011 | LaRose et al. |
| 8,002,518 | B2 | 8/2011 | Woodard et al. |
| 8,007,254 | B2 | 8/2011 | LaRose et al. |
| 8,088,059 | B2 | 1/2012 | Jarvik |
| 8,114,008 | B2 | 2/2012 | Hidaka et al. |
| 8,123,503 | B2 | 2/2012 | Shinshi et al. |
| 8,123,670 | B2 | 2/2012 | Bokeriya et al. |
| RE43,299 | E | 4/2012 | Siess |
| 8,152,493 | B2 | 4/2012 | LaRose et al. |
| 8,157,539 | B2 | 4/2012 | Hidaka et al. |
| 8,177,703 | B2 | 5/2012 | Smith et al. |
| 8,210,829 | B2 | 7/2012 | Horvath et al. |
| 8,226,373 | B2 | 7/2012 | Yaegashi |
| 8,282,359 | B2 | 10/2012 | Ayre et al. |
| 2003/0124007 | A1 | 7/2003 | Schima et al. |
| 2008/0262289 | A1 | 10/2008 | Goldowsky |
| 2010/0174131 | A1 | 7/2010 | Foster et al. |
| 2011/0238172 | A1 | 9/2011 | Akdis |
| 2011/0257462 | A1* | 10/2011 | Rodefeld ................. A61F 2/01 600/16 |
| 2012/0035411 | A1 | 2/2012 | LaRose et al. |
| 2012/0041255 | A1 | 2/2012 | Delgado, III |
| 2012/0053392 | A1 | 3/2012 | Kung |
| 2012/0059212 | A1 | 3/2012 | LaRose et al. |
| 2012/0059213 | A1 | 3/2012 | Spence |
| 2012/0059214 | A1 | 3/2012 | Zhou |
| 2012/0065457 | A1 | 3/2012 | Peters et al. |
| 2012/0078030 | A1 | 3/2012 | Bourque |
| 2012/0078031 | A1 | 3/2012 | Burke et al. |
| 2012/0078032 | A1 | 3/2012 | Spence |
| 2012/0078033 | A1 | 3/2012 | Mohl |
| 2012/0088954 | A1 | 4/2012 | Foster |
| 2012/0089225 | A1 | 4/2012 | Akkerman et al. |
| 2012/0095280 | A1 | 4/2012 | Timms |
| 2012/0095281 | A1 | 4/2012 | Reichenbach et al. |
| 2012/0130152 | A1 | 5/2012 | Ozaki et al. |
| 2012/0134793 | A1 | 5/2012 | Wu et al. |
| 2012/0134832 | A1 | 5/2012 | Wu |
| 2012/0142994 | A1 | 6/2012 | Toellner |
| 2012/0142995 | A1 | 6/2012 | Tao et al. |
| 2012/0149970 | A1 | 6/2012 | Jeevanandam et al. |
| 2012/0149971 | A1 | 6/2012 | Jeevanandam et al. |
| 2012/0172654 | A1 | 7/2012 | Bates |
| 2012/0172655 | A1 | 7/2012 | Campbell et al. |
| 2012/0172656 | A1 | 7/2012 | Walters et al. |
| 2012/0172657 | A1 | 7/2012 | Marseille et al. |
| 2012/0178985 | A1 | 7/2012 | Walters et al. |
| 2012/0178986 | A1 | 7/2012 | Campbell et al. |
| 2012/0203056 | A1 | 8/2012 | Corbett |
| 2012/0220816 | A1 | 8/2012 | Peters et al. |
| 2012/0226096 | A1 | 9/2012 | Callaway et al. |
| 2012/0226097 | A1 | 9/2012 | Smith et al. |
| 2012/0226350 | A1 | 9/2012 | Rudser et al. |
| 2012/0232331 | A1 | 9/2012 | Nour |
| 2012/0237353 | A1 | 9/2012 | Schumacher et al. |
| 2012/0245404 | A1 | 9/2012 | Smith et al. |
| 2012/0245405 | A1 | 9/2012 | Tatum et al. |
| 2012/0253103 | A1 | 10/2012 | Robert |
| 2012/0259157 | A9 | 10/2012 | Spence |
| 2012/0265002 | A1 | 10/2012 | Roehn et al. |
| 2012/0265004 | A1 | 10/2012 | Kaushansky |
| 2012/0271096 | A1 | 10/2012 | Gelbart et al. |
| 2012/0277520 | A1 | 11/2012 | Duncan |
| 2012/0283506 | A1 | 11/2012 | Meister et al. |
| 2012/0283507 | A1 | 11/2012 | Lillehei |
| 2012/0289765 | A1 | 11/2012 | Kaushansky et al. |
| 2012/0296152 | A1 | 11/2012 | Reichenbach et al. |

FOREIGN PATENT DOCUMENTS

| | | |
|---|---|---|
| EP | 1727988 | 7/2011 |
| EP | 2405140 | 1/2012 |
| EP | 2405141 | 1/2012 |
| EP | 2407186 | 1/2012 |
| EP | 2407188 | 1/2012 |
| EP | 2461465 | 6/2012 |
| EP | 2218469 | 10/2012 |
| EP | 1618905 | 11/2012 |
| JP | H07504015 | 4/1995 |
| JP | 2001514532 | 9/2001 |
| JP | 2007506027 | 3/2007 |
| WO | 9409274 | 4/1994 |
| WO | 9413955 | 6/1994 |
| WO | 9749440 | 12/1997 |
| WO | 0071184 | 11/2000 |
| WO | 200502800 | 3/2005 |
| WO | 2005020848 | 3/2005 |
| WO | 2005090791 | 9/2005 |
| WO | 2006096049 | 9/2006 |
| WO | 2008017289 | 2/2008 |
| WO | 2009019017 | 2/2009 |
| WO | 2010036815 | 4/2010 |
| WO | 2010118475 | 10/2010 |
| WO | 2010118476 | 10/2010 |
| WO | 2010119267 | 10/2010 |
| WO | 2010126503 | 11/2010 |
| WO | 2010132451 | 11/2010 |
| WO | 2010135279 | 11/2010 |
| WO | 2010149408 | 12/2010 |
| WO | 2011050279 | 4/2011 |
| WO | 2011056980 | 5/2011 |
| WO | 2011069109 | 6/2011 |
| WO | 2011081626 | 7/2011 |
| WO | 2011109747 | 9/2011 |
| WO | 2012047550 | 4/2012 |
| WO | 2012135495 | 10/2012 |

OTHER PUBLICATIONS

International Search Report and Written Opinion, PCT/US2012/067648 dated Mar. 25, 2013.
Extended European Search Report issued in EP 12853143.1 dated Jul. 14, 2015.

(56) References Cited

OTHER PUBLICATIONS

International Preliminary Report on Patentability, PCT/US2012/067648 dated Jun. 12, 2014.
AU Serial No. 2012345572, Exam Report No. 1, 4 pages dated Dec. 12, 2016.
EP Serial No. 12 853 143.1, EPO Communicaiton under Rule 71(3), 7 pages, dated Oct. 14, 2016.
EP Serial No. 15202083.0, EPO extended Search Report, 8 pages, dated Jun. 17, 2016.
Response to European Search Report filed in EP 12853143.1 dated Feb. 10, 2016, 14 pgs.
JP Office Action, Serial No. dated Sep. 28, 2016 (including English translation), 22 pgs.

* cited by examiner

CAVOPULMONARY VISCOUS IMPELLER ASSIST DEVICE AND METHOD

CROSS REFERENCE TO RELATED APPLICATIONS

This application claims the benefit of priority to U.S. Provisional Patent Application Ser. No. 61/566,616, filed Dec. 3, 2011, titled CHRONIC CAVOPULMONARY ASSIST DEVICE AND METHOD, and U.S. Provisional Patent Application Ser. No. 61/611,947, filed Mar. 16, 2012, titled CAVOPULMONARY VISCOUS IMPELLER ASSIST DEVICE AND METHOD, both of which are incorporated herein by reference.

FIELD OF THE INVENTION

Various embodiments of the invention relate generally to the field of pumps including blood pumps, including non-positive displacement pumps of rotary design, and including those suitable for permanent implantation in animals for use in circulatory support.

BACKGROUND OF THE INVENTION

Some children are born missing half their heart. Known as single ventricle heart disease, it is the leading cause of death in children less than one year of age from any structural birth defect. One common anatomic variant is Hypoplastic Left Heart Syndrome. Until recently this condition was not compatible with survival. Beginning in the 1970's, developments in the surgical treatment of single ventricle heart disease have resulted in a means of not only survival, but also reasonable quality of life for survivors at least into early adulthood. Current therapy includes a series of 3 staged open heart procedures. While these procedures offer hope for survival, they remain problematic and notorious for instability and mortality. The staged surgical reconstruction of the circulatory system culminates in a univentricular Fontan circulation, eponymous with Dr. Francis Fontan who first described the repair in 1971.

In a univentricular Fontan circulation, the single ventricle (pumping chamber) is committed to provide blood flow to the body. Opposed to a normal 2-ventricle circulation, however, blood flow through the lungs is not supported by a ventricular power source; it should rather flow through the lungs passively. Therefore, the motive force for blood flow through the lungs rests upon systemic venous pressure alone. As a consequence, systemic venous pressure is markedly elevated and systemic venous return is significantly altered. This sets up a new set of hemodynamic problems, described by de Leval as the Fontan paradox, in which elevated systemic venous pressure coexists with relative pulmonary arterial hypotension. Preload to the single ventricle is reduced, as well as cardiac output. Patients with a univentricular Fontan circulation are therefore at high risk for late Fontan failure and attrition.

The late consequences of this circulatory arrangement are now an emerging public health concern. Thousands of patients who survive Fontan palliation are expected to present with Fontan failure. The insidious complications of chronically elevated systemic venous pressure include hepatic and gut dysfunction, protein losing enteropathy, leg swelling, and collection of fluid in the abdominal and chest cavities. The insidious complications of chronically reduced preload include late ventricular diastolic dysfunction, and poor systemic tissue perfusion. Targeted medical therapeutic options for Fontan failure do not exist. For example, while diuretic therapy may improve symptoms of increased tissue/organ edema, it does so at the expense of circulating blood volume which is helpful to Fontan circulatory homeostasis. Similarly, although the use of inotropic support may improve myocardial contractility, this is of marginal impact in an insufficiently filled ventricle. Heart transplantation is a poor end-stage option: Transplantation carries morbidity of its own, and the donor pool is limited. Few patients will ultimately be candidates or receive a donor organ for transplantation.

The development of a permanent right-sided circulatory support device directly addresses the Fontan paradox and will improve late quality of life and outcomes for those born with single functional ventricle. One aspect of some embodiments has been to include power sources to support the univentricular Fontan circulation. The placement of a power source at the level of the total cavopulmonary connection effectively empowers the univentricular Fontan circulation by placing a right ventricle equivalent back into a circulation that lacks one. By simultaneously reducing systemic venous pressure and improving ventricular preload, normal 2-ventricle physiology can be effectively restored.

Prior applications of existing blood pump technology have been contemplated to address the problem of powering the Fontan circulation. These have consisted primarily of applying intravascular unidirectional axial flow pumps to augment Fontan flow. The concept of cavopulmonary assist was introduced in 2003 with the simultaneous use of 2 unidirectional axial flow pumps (Rodefeld et al, Ann Thoracic Surg). This has limitations, however, as one-way flow devices will cause undesirable back-pressure elevation in the opposing vena caval territory. Other groups have followed with modifications of axial flow pump designs intended to operate in the low-pressure systemic venous circulation. This has also included a modification of the preferred TCPC Fontan venous pathway to a 3-way pathway so that the pathway better accommodates a unidirectional pump in a common unidirectional outflow limb. Although in theory this is possible, the 3-way vascular configuration is not the preferred hemodynamic pathway in an unsupported Fontan circulation.

What follows are various improvements in the field of non-positive displacement circulatory pumps that overcome some of the disadvantages of existing systems.

SUMMARY OF THE INVENTION

Accordingly, it is an aspect of some embodiments to provide an improved rotary blood pump which will support the univentricular Fontan circulation on a permanent basis;

It is a further aspect of some embodiments to provide a blood pump in which the rotor is external to the stator;

It is a further aspect of some embodiments to provide a means for pumping blood or other liquids having a bearingless and sealless design;

It is a further aspect of some embodiments to provide a means for pumping blood or other liquids using a rotary impeller located in the midst to the bloodstream or the fluid passageway;

it is still a further aspect of some embodiments to provide a means for pumping blood or other liquids that does not use a positive displacement pumping arrangement;

If is a further aspect of some embodiments to provide a compact rotary blood pump which has no potential to obstruct the blood flow pathway or the fluid passageway;

It is a further aspect of some embodiments to provide a rotary pump which uses blood or the pumped fluid as a bearing material;

It is a further aspect of some embodiments to provide a rotary pump which uses passive magnetic bearings to suspend the rotating element in a radial and axial fashion;

It is a further aspect of some embodiments to provide hydrodynamic and thrust bearings in an arrangement in the event of touchdown due to device external shock or imbalanced operation;

It is a further aspect of some embodiments to provide a permanent Fontan pump which will afford the opportunity to address right/left lung blood flow disparity;

It is a further aspect of some embodiments to provide a permanent Fontan blood pump which will afford the opportunity to address vessel stenoses at the time of device implantation.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

DESCRIPTION OF THE PREFERRED EMBODIMENT

Figure 1A:
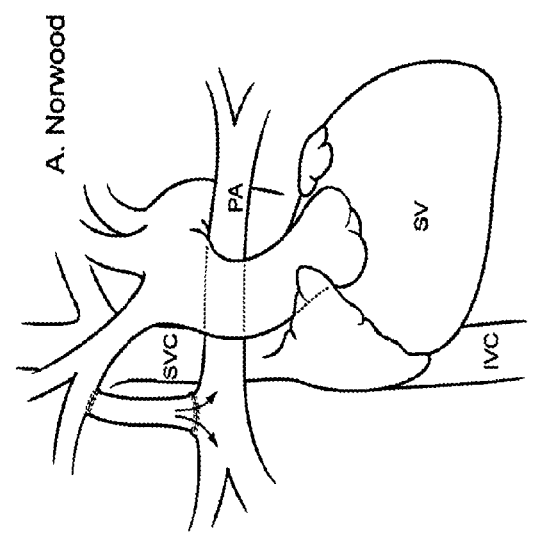
FIGS. 1A, 1B, and 1C are schematic representations of a known surgical method.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims.

The use of an N-series prefix for an element number (NXX.XX) refers to an element that is the same as the non-prefixed element (XX.XX), except as shown and described thereafter The usage of words indicating preference, such as "preferably," refers to features and aspects that are present in at least one embodiment, but which are optional for some embodiments. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. This description convention also applies to the use of prime ('), double prime ("), and triple prime ("') suffixed element numbers. Therefore, it is not necessary to describe the features of 20.1, 20.1', 20.1", and 20.1"' that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

In the text and drawings of this document reference will be made to the use of a pump in the circulatory system of an animal. It is recognized still further that the apparatus and methods described herein further pertain to the pumping of a fluid in any similar arrangement of fluid passageways.

Various embodiments of the present invention pertain to a pump adapted and configured to provide a pressure assist to the cavopulmonary system of an animal. Preferably, the pump is motorized and provided with electrical power from a source outside of the animal. In some embodiments, the pump is packaged within a housing that is adapted and configured to be placed within the circulatory system of the animal on a permanent basis.

In some embodiments, the pump is of the non-positive displacement variety, and provides an increase in energy to the pump fluid by centrifugal action. Preferably, the centrifugal assist is applied to the working fluid by a viscous operation on the surface of a rotating element. In some embodiments, the rotating element is axisymmetrical, whereas in other embodiments the rotor is both axisymmetrical, and further symmetrical about a plane.

Some embodiments include a rotor that is suspended about an internal stator by magnetic bearings or hydrodynamic bearings, or a combination of the two. In those embodiments having both axial and planar symmetry, there is little or no net thrust of the rotor relative to the stator, and the negligible net thrust can be accommodated by the hydrodynamic bearings. In some embodiments, the magnetic bearings are adapted and configured to provide both radial support and further a magnetic force that is resistive to any net thrust. These magnetic thrust bearings can include a second pair of magnetic bearings, in additional to a first pair of magnetic bearings that provide radial support of the rotor. In those embodiments in which the stator has a shape for viscously and centrifugally imparting energy to the fluid (such as a VIP pump), the first pair of magnetic bearings providing radial support may be located proximate to the opposing ends of the rotor, where the outer shape of the rotor is a relatively more parallel to the rotational axis. The second paramagnetic bearings providing thrust support may be located proximate to the center of such a rotor, where the outer shape of the rotor is relatively more parallel to a central plane of symmetry.

In some embodiments the rotating element has the general shape adapted and configured for providing viscous and central focal action to the fluid, and further with both axial and planar symmetry. In some of these embodiments, the rotor comprises a thin-walled shell of a suitable biocompatible material. This rotor can be formed by any means, including, such as by die forming or forging of sheet metal. In still further embodiments, the rotor may be of a two-part construction, and having a joining split line located along the central plane or along the rotational axis.

Pumps according some embodiments of the present invention include stators having an external shape that is substantially the same as the internal shape of the rotor. In such embodiments, the close gap between the rotating and static members can be provided with a cushioning fluid, such as the fluid being pumped by the rotor. In those embodiments in which the rotor is a thin-walled shell, the outer surface of the stator can have substantially the same shape as the external shape of the rotor, and in those embodiments in which the rotor has VIP pumping characteristics, likewise the bearing flowpath between rotor and stator can have VIP pumping characteristics. For those pumps adapted and configured to pump blood in circulatory system of an animal, the size and configuration of the separating gap is adapted and configured to discourage clotting of the blood within the gap.

The bioengineering considerations to accomplish cavopulmonary assist are unique in a univentricular Fontan circulation. A chronic Fontan pump should: 1) deliver low pressure, high volume flow similar to normal right ventricular hemodynamics; 2) augment flow in 4 directions with axially opposed inflow and orthogonally related bidirectional outflow; 3) avoid thrombogenicity, preferably with a bearingless and sealless design; 4) have an expected durability of decades; 5) utilize a power source that is realistic for such long-term use; 6) should not obstruct flow in the Fontan venous pathway—whether the pump is functional or not.

A chronic rotary blood pump according to one embodiment of the present invention designed to support the Fontan circulation is surgically implanted into the total cavopulmonary connection (TCPC). This is the anatomic junction created between the superior and inferior vena cavae and the right and left pulmonary arteries during Fontan surgery. This anatomic configuration is in the shape of a '+' and is the preferred construction for passive venopulmonary blood flow in Fontan patients. The surgical implantation of a permanent cavopulmonary assist device in this location is technically similar to a Fontan conversion operation, and therefore reasonable to perform. It includes cardiopulmonary bypass, but not cardioplegic arrest. Once implanted, the pump provides 2-5 mmHg pressure augmentation to Fontan venous flow. Accordingly, this decreases upstream systemic venous pressure by 2-5 mmHg, and increases pulmonary arterial pressure by 2-5 mmHg, translating to increased transpulmonary blood flow, increased preload, and ultimately increased cardiac output. This low pressure pumping action provides a transformative improvement in circulatory status by restoring more stable 2-ventricle physiology.

One embodiment of the invention disclosed herein solves these problems. The pump (20, 120) disclosed is designed to permanently augment Fontan venous flow. It is modeled morphologically after the temporary percutaneous expandable von Karman viscous impeller pump which is further described in copending U.S. patent application Ser. No. 13/122,797, filed Apr. 6, 2011, and titled ACTIVE OR PASSIVE ASSISTANCE IN THE CIRCULATORY SYSTEM. This permanent pump concept is based a spinning disk configuration in the shape of a 2-sided centrifugal pump. For some embodiments of the permanent pump disclosed here, however, the impeller can be rigid: It is not required to expand (open) and contract (close). The rotating impeller (40, 140), suspended in the midst of the pump housing (30, 130), draws fluid in from the axial direction (superior and inferior vena cava) and pumps it to the outlets (33, 133) which lead to the left and right lungs. A single pump effectively produces a 4-way pumping action which is useful to augment Fontan TCPC flow. Preliminary designs have been demonstrated and published to induce pressure differential of 2-10 mmHg in the nominal operating range (3-7K RPM, with capabilities of generating higher pressure (up to 40 mmHg) at higher rotational speeds in the unlikely event of pulmonary hypertension). Further, the pump has no potential to obstruct flow in the Fontan venous pathway. Even when non-rotational, the impeller continues to serve a streamlining function to passive flow through the TCPC, reducing the hydraulic energy loss within the 4-way junction.

Some embodiments use an electrical motor design which uses an "inside-out" configuration: A blood pump is disclosed in which the central stator is stationary and the rotor revolves externally around it. This configuration is used in brushless DC motors for CD-ROM hard drive computer hard disks. When the central stator windings are electronically activated, a magnetic rotor drum with passive magnetic elements is induced to rotate around the stator. This type of electrical motor is also widely used in the remote controlled aircraft hobby for high torque at lower speeds, a compact size, a high power to weight ratio, and high efficiency.

In a Fontan pump, the use of this configuration resolves the fluid flow gap problem. The magnetic flux gap between rotor and stator is at a normal distance for electromechanical actuation, allowing for electromagnetic power transmission. At the same time, this leaves the blood flow path between impeller and housing unobstructed because the housing is no longer integral to electrical operation of the pump. The pump external housing does not necessarily include electronic components. It retains a low profile and is dedicated to function as a flow conduit to the inlet and outlet blood vessels. The motor is contained within the center of the impeller, in the midst of the blood stream.

In one embodiment, an inside-out polyphase motor configuration is disclosed as means for it electromagnetically coupling in internal stator and in external rotor, which allows the pump housing to be unencumbered with electromechanical drive components. The rotor and stator are centrally located within the pump housing. At least a portion of the stator is located within the interior of the rotor. The housing serves as a shell to direct inflow and outflow in a predetermined manner. This provides the aspect of narrow radial width of the outer shell of this viscous pump as compared to more traditional centrifugal pumps. The new design is therefore compatible with intravascular and intracardiac pumping applications because the risk of flowpath obstruction is decreased. This inside-out motor design is similar to outrunner electrical BLDC motors used in CD-ROM drives and in the remote control airplane hobby. These motors have an externally rotating drum as the rotor with a central stationary stator. An aspect of this is that they provide higher torque and lower rotational speed than more traditional inrunner electrical motor designs. Although the use of a brushless DC motor is shown and described herein, yet other embodiments of the present invention contemplate other means for electromagnetically coupling the rotor and stator.

A blood pump disclosed according to one embodiment has a central shaft (62, 162) which is immobilized and fixed to the external housing. A strut spider (34,134) at each inlet (32, 132) end provides rigid structural support to the shaft ends. Between the spider and the center of the shaft, a series of sequential passive magnetic bearings (66, 166) are present, including a plurality of permanent ring magnets and pole pieces which radially suspend the rotor around the shaft in the configuration of a Halbach Array. In the central region of the shaft, a ferrite radial stator (60,160) is permanently affixed. The core stator in some embodiments is comprised of iron or other suitably magnetic materials, and in some embodiments has 9-12 poles with windings which generate electromechanical force. The central shaft which contains the stator and passive magnetic bearing supports for the rotor is sealed and has no moving mechanical parts.

A rotor in some embodiments form-fits to surround the central shaft and stator. Preferably fabricated of 2 halves which are joined as a unitary component, the rotor contains a circular passive magnetic ring or drum built in its central region which is circumferentially adjacent to the stator heads and at a predetermined gap from the stator heads. The magnetic ring is induced to revolve around the stator with electrical activation and commutation, thereby revolving the rotor body around the central stator.

The outer surface of the rotor is at a predetermined shape and acts as the blood contacting surface and induces flow. The rotor is magnetically suspended from the shaft by passive magnetic bearings on both sides of the center, and is further supported by a squeeze film effect of blood which is pumped within the gap. The inlet (84a, 184a) for the blood film is located on the inlet ends of the shaft where the rotor axial ends are located. The outlet (84b, 184b) for the blood film is located at or near the rotor outflow edge. A pumping action for the thin film blood is provided by centrifugal force. This allows for fresh blood to constantly flush through the gap and prevent clot formation within the gap. The gap surfaces create fluid pressure in the rotor-stator gap thereby imparting radially symmetrical forces to the rotor, which maintains the radial position of the rotor within the impeller when the rotor is spinning. Hydrodynamic journal bearing pads on the shaft are present as touchdown backup bearings in the event of shock to the pump sufficient to cause a touch-down event between the rotor and stator. The rotor is not actively electrified, nor does it have any moving or mechanical sub components.

The rotor revolves around the axis of the shaft in a bearingless and sealless fashion. The interface between rotor and stator incorporates a predetermined gap which allows a layer of blood to provide rotor damping and to induce a squeeze film hydrodynamic layer of blood to serve as a fluid bearing and lubricant to rotor operation. The interface is preferably devoid of seams, crevices, or sharp angulations unless specifically intended which may lead to clot formation due to stagnation of flow or zones of high shear stress. A series of passive magnetic bearing structures within the shaft and the rotor (radial bearing support), and possibly centrally (axial bearing support) near the location of the stator head provides passive magnetic levitation of the rotor above the stator. Blood which flows into the inlet gap between rotor and stator have an outflow in the trailing edge of the rotor, allowing constant flow and replenishment of fresh blood within the gap to provide lubrication for rotor motion.

The rotor-stator gap (79, 179) architecture may include widening or narrowing of the gap at certain locations to allow a wedge effect for the blood circulating within the gap to improve biocompatibility, stability, and thrombogenicity resistance. Some embodiments include hydrodynamic bearing design such as a wedge shape integral to the design to compress fluid into a high pressure thin gap flow in strategic locations which aids in hydrodynamic lubrication and stabilization of rotating interfaces.

The location of the rotor/impeller in the midst of the blood stream and continuous flushing of the gap between stator (60, 160) and rotor (80, 180) allow for dissipation of the heat generated from the electrical energy expended in powering the pump. The low profile of the housing causes minimal disruption to adjacent organs. The large fluid gap maintained between impeller and housing minimizes risk of blood flow obstruction in the event of device malfunction.

The outer surface of the rotor has a predetermined shape roughly similar to a 2-sided conical disk. This surface serves as the primary blood contacting region. Rotation results in 4-direction flow augmentation. The surface may be modified with surface vane structure in any arrangement including but not exclusive to straight vanes, curved vanes, variable height vanes, protruding vanes, channel vanes—generally intended to optimize pump hydraulic performance. This may include differential expression of surface vane structure on one side of the impeller. The geometry of the impeller may also take any shape or form to perform specified pumping actions. This may include symmetric impeller geometry or asymmetric impeller geometry. Impeller asymmetry may be useful for example in pumping blood in a 3-way configuration such as a blood vessel bifurcation.

The power source for the pump includes a wire and electronic controller unit which is located remotely from the pump body. The controller unit is located in a subcutaneous position for transcutaneous interrogation, programming, and monitoring. Feedback on pump performance to the controller is derived from back-EMF sensing. The sampled back EMF provides electronic commutation control as well as an error signal indicative of the positional error of the rotor. The wires connecting the controller to the pump enters through the wall of the pump body at the location of a spider strut, travel through a spider limb to the stator shaft, and from there to the stator ferrite core and windings. The power source to the controller can be either by a percutaneous wire which attaches directly to an external power source, or by any transcutaneous power transmission technology which avoids a wire exiting from the skin of the body wall.

The external housing of the pump has arm extensions from each inlet and outlet which are seamlessly bonded to the rigid housing body. These extensions, possibly made of expanded polytetrafluoroethylene (ePTFE), can be surgically tailored by the implanting surgeon. This allows the surgeon to address any offset of the superior and inferior vena cava during the implantation procedure. Because both inlets lead to a central fixed impeller and housing, uniform mixing and equal distribution of SVC and IVC derived blood is distributed to the right and left lungs. This is helpful due to the problem of unequal flow distribution of hepatic venous effluent to the lungs, and the lack of hepatic factor leading to the formation of arteriovenous malformations in the deprived lung. The adjustable limbs allow the surgeon to address any blood vessel stenoses or length disparities which may exist in the patient as a consequence of prior surgical procedures. It allows the inferior vena caval limb to be carried to the level of the diaphragm for an extracardiac replacement of a previously placed Fontan conduit.

This disclosure has a number of aspects. It can provide a permanent blood pump concept for mechanical circulatory support of the univentricular Fontan circulation. It can provide electrical motor drive for rotary blood pumps where the motor design is inside-out. This allows the impeller to be placed in the midst of the bloodstream, with a flux gap appropriate for a brushless DC motor drive system. The outer housing functions as a passive directional flow conduit function. This reduces the bulk of the device, and allows for a large blood flow gap to exist between the impeller and housing, reducing or eliminating the possibility of blood flow obstruction in the event of device mechanical failure. With this, blood pumps can be more readily implanted into the bloodstream, whereas related art devices include paracardiac or para-vascular placement.

Figure 1B:
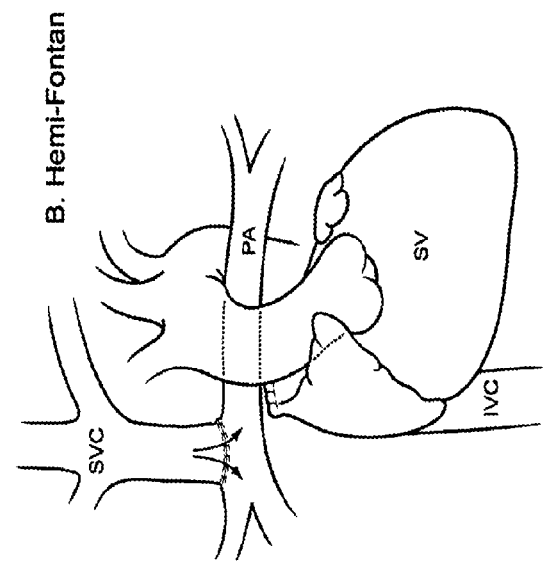
Figure 1C:
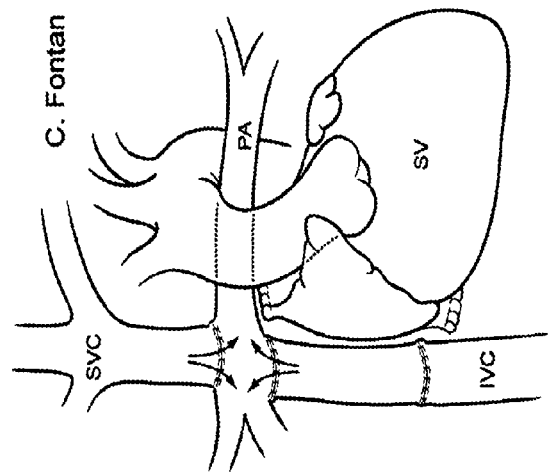

With regards to FIGS. 1a, 1b, and 1c there are shown several stages of repair to a heart having a univentricular congenital defect. In the most common form, Hypoplastic Left Heart Syndrome, the left ventricle fails to form in a way that is ever functional. In the first procedure, which must be performed in the first weeks of life, the right ventricle is converted to pump blood to the body rather than to the lungs (FIG. 1a). Blood flow to the lungs must be secondarily derived from a high-pressure systemic arterial source via a systemic-to-pulmonary arterial shunt to overcome the potential for elevated pulmonary vascular resistance (PVR) in newborns. Unfortunately, the use of a shunt results in severe hypoxemia and creates an inherently unstable parallel arrangement of the systemic and pulmonary circulations which must be delicately balanced. Consequently, this procedure is notorious for instability and mortality of 20 to 30%. Inter-stage mortality (between $1^{st}$- and $2^{nd}$-stages) is also exceedingly high (4-24%). This high risk of death is a manifestation of an inherently unstable circulation, for which the shunt is the common denominator. Decompensation is characteristically sudden, unpredicted, and without discernible cause. In contrast, stability and survival after the second- and third-stage operations is much better, which coincides with takedown of the shunt.

At the expense of providing a reliable source of pulmonary blood flow, the shunt creates 4 potentially lethal physiologic consequences: the single ventricle must (1) support both pulmonary and systemic circulations in an unstable parallel arrangement by (2) pumping twice normal volume, and perform this doubled workload under the harsh conditions of (3) severe hypoxemia ($PaO_2$ 30-40 mmHg) and (4) impaired myocardial coronary perfusion due to (a) decreased diastolic blood pressure from shunt run-off and (b) increased myocardial wall tension due to ventricular volume overload. Synthetic shunts also have risk of lethal thrombosis. Any change affecting the balance of the parallel circulations requires compensation elsewhere to restore equilibrium. Dangerous positive physiologic feedback loops escalate instability: Hypoxemia leads to lung hypoperfusion, and thus worsening hypoxemia; conversely, "high" $PaO_2$ (>40 mmHg) dilates the pulmonary circulation, leading to lung overperfusion and further elevation of $PaO_2$— at the expense of systemic perfusion. Life-saving management may require counterintuitive and harmful intervention, including further reduction of inspired oxygen (at times below 0.21) and hypoventilation. Not surprisingly, neurocognitive impairment subsequent to Stage-1 repair is common. Paradoxically, the shunt induces and exacerbates the conditions that mandate its use in the first place: hypoxic pulmonary vasoconstriction and pulmonary hypertension. These impair postnatal pulmonary vascular maturation, and elevate early and late basal PVR which impair subsequent Fontan status. Ironically, shunt physiology may make the timing for Stage-2 conversion later than it might be otherwise, and may worsen candidacy for stage-2 and -3 Fontan conversion.

The second and third operations (FIGS. 1b and 1c collectively) represent "staged Fontan conversion". The problematic shunt is disconnected, and blood flow to the lungs is converted to a low pressure systemic venous source by connecting the vena cavae directly to the pulmonary arteries (a cavopulmonary connection). Blood flow to the lungs and body is restored to a more stable series arrangement, as found in normal two-ventricle physiology. However, the sole energy source for pulmonary blood flow is relegated to systemic venous pressure, which must be significantly elevated (10-15 mmHg) in order for flow to occur. This introduces two new problems which are responsible for the majority of Fontan-related health concerns: 1) systemic venous hypertension, and 2) suboptimal ventricular filling and cardiac output. In the second operation (FIG. 1b), the superior vena cava (SVC) is connected to the pulmonary artery as the sole source of pulmonary blood flow. This stage is typically performed beyond 4 months of age, when the risk of elevated pulmonary vascular resistance is low. Inferior vena caval (IVC) flow continues into the common atrium, leaving a significant right-to-left shunt and hypoxemia, which continues to exacerbate pulmonary hypertension. Pulmonary blood flow is transitioned to nonpulsatile, steady-flow perfusion, which increases pulmonary vascular impedance.

In the third operation (FIG. 1c), IVC (and thus total) venous return is diverted to the pulmonary arteries. The lower half of the body and the splanchnic circulation are exposed to elevated venous pressure. Marginal candidates, in whom IVC pressure exceeds 12-15 mmHg, may suffer from low cardiac output, impaired hepatic function, and develop ascites and effusions. The ideal age and timing for this stage is unknown and varies amongst institutions.

Figure 2A:
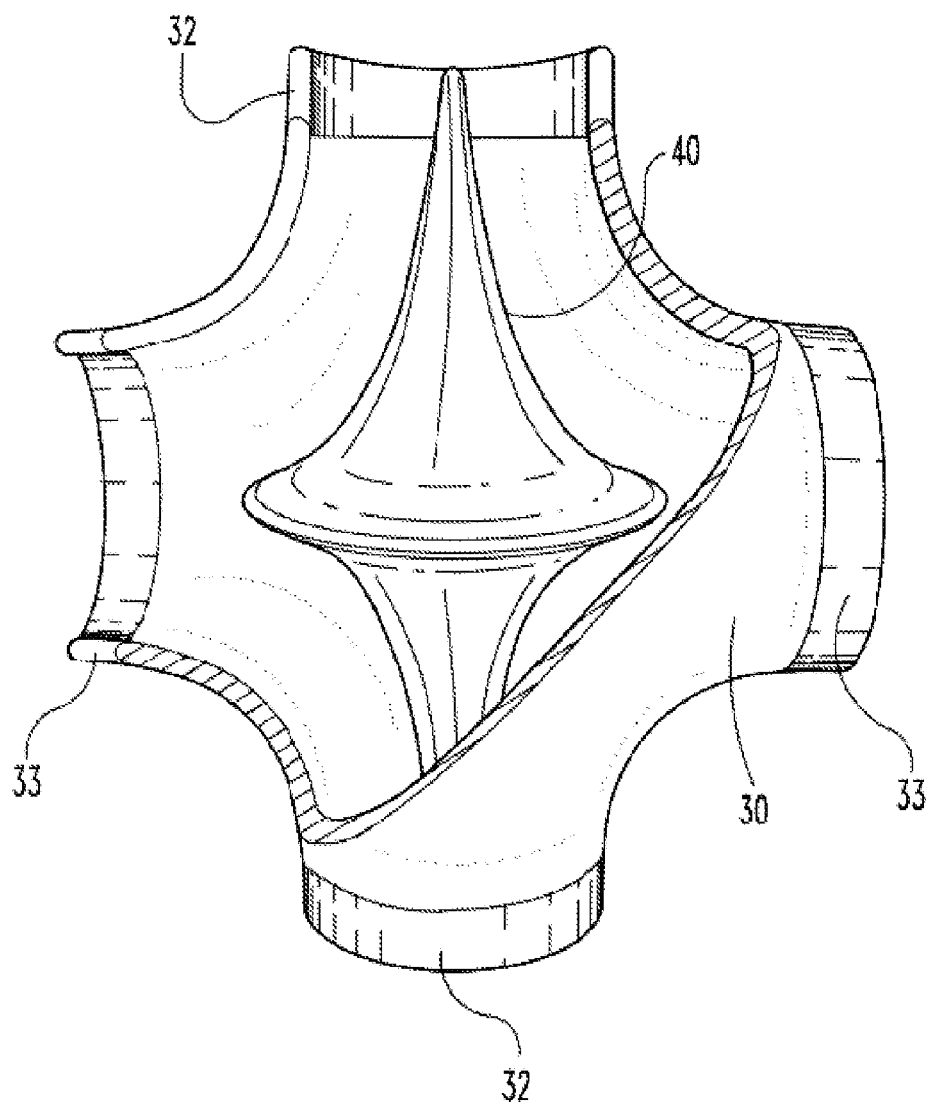
FIG. 2A is a front elevational view in partial cutaway of a pump according to one embodiment of the present invention, the pump being represented with shaded surfaces, and with some structure removed for improved clarity.
Figure 2B:
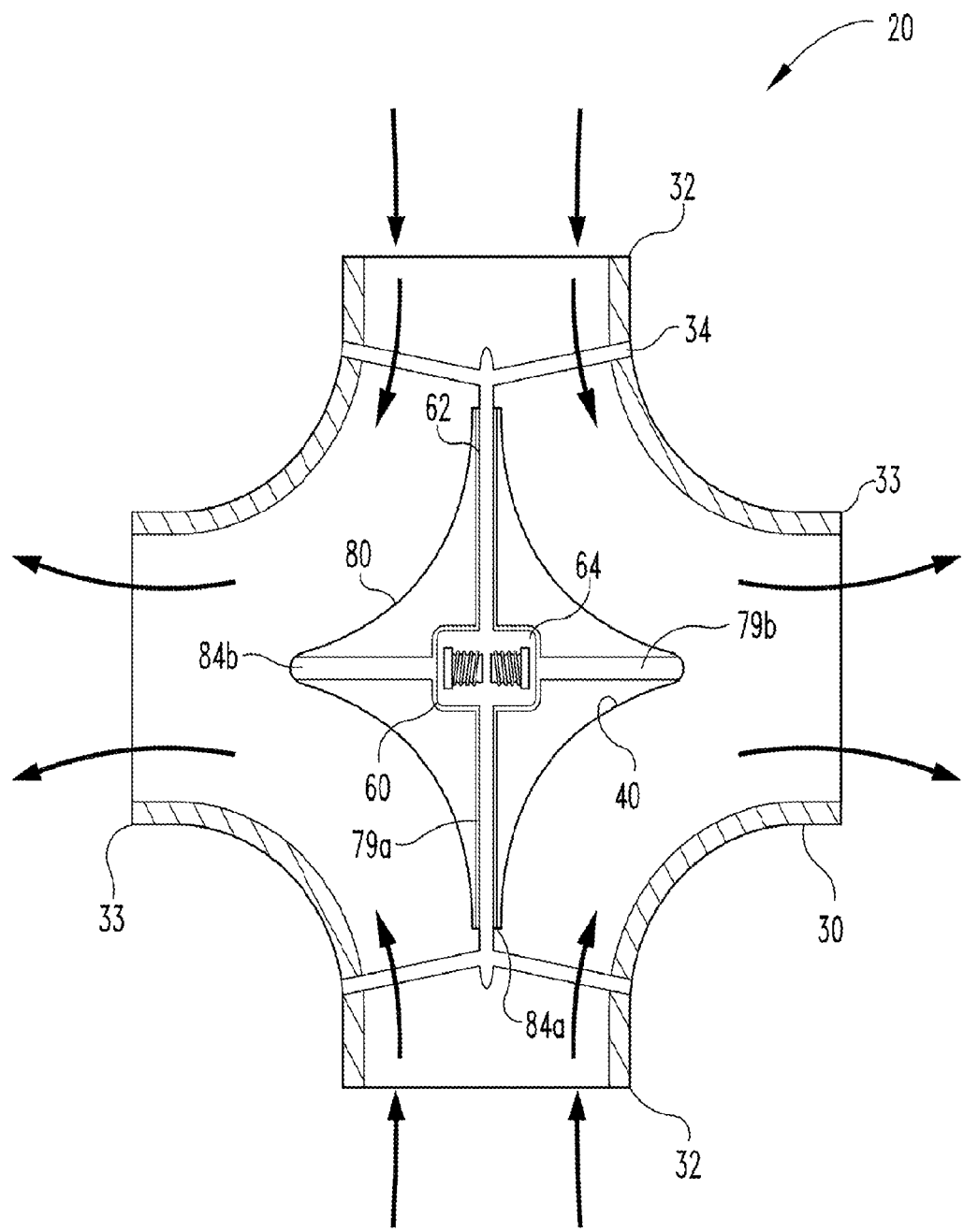
FIG. 2B is a front elevational view in partial cutaway of a pump according to another embodiment of the present invention, with portions of the rotor and stator being in cutaway, with the structure schematically restored

In accordance with some of the illustrative embodiments of the present invention, and referring to FIGS. 2A and 2B, a rotary blood pump 20 includes a housing 30 and an impeller 40. The impeller includes a central stator core 60 and surrounding rotor 80. The central stator core includes a shaft 62 and a rotary magnetic core array of windings 64 which are electronically controlled. The impeller is rigidly suspended within the housing by non-obstructive and hydrodynamic spider struts 34 at each end of the spindle, although in some embodiments the struts 34 are adapted and configured to provide some amount of flexibility in response to centrifugal and dynamic loads imposed on or by pump 20.

The housing 30 includes a flow diverting shell enclosing the impeller. The housing design is predetermined to optimize flow and distribute the fluid energy from the impeller so that flow has minimal turbulence and pressure loss within the pump. The housing preferably includes multiple inlet 32 and outlet 33 sections, although yet other embodiments contemplate "T" shaped housings having a pair of inlets and a single outlet, or a pair of outlets and a single inlet. The housing may have a scroll shaped volute in the outlets to optimize outflow patterns. The housing maintains a generally rigid and fixed spatial relationship between the impeller surface and the housing surface. The inlet and outlet ends of the housing are composed of a biocompatible malleable plastic which can be sutured to blood vessels during installation of the pump.

Referring to FIG. 2B, it can be seen that an annular gap 84 is provided between stator 60 and rotor 80. As rotor 80 spins, a viscous pumping action occurs along the outer surface, inducing flow from inlets 32 toward outlets 33. This flow across the outer surface of stator 80 has a reduced static pressure proximate to flow exit 84b. Because of this reduced outlet pressure (and in some embodiments, also due to the possibility of configuring inlet annulus 84a for an increased static pressure) flow occurs within bearing flowpath 79. This flow provides a hydrodynamic cushioning to rotor 80. Flow extends along the exterior of shaft 62, and then flows radially outward past the central portion of the stator that houses the windings, and finally out of an expulsion line 79b to exit orifice 84b.

It can be seen in FIG. 2B that the windings 64 are adapted and configured to provide a torque to rotor 80 relative to stator 60, by way of interaction with a plurality of permanent magnets 81 embedded in rotor 80. In one embodiment magnets 81 include a plurality of permanent magnets, circumferentially embedded within rotor 80. Windings 64 are provided with a rotating magnetic field by way of electrical leads 68 that receive electrical power from a source that is operatively controlled by a controller such as a digital computer.

Figure 2C:
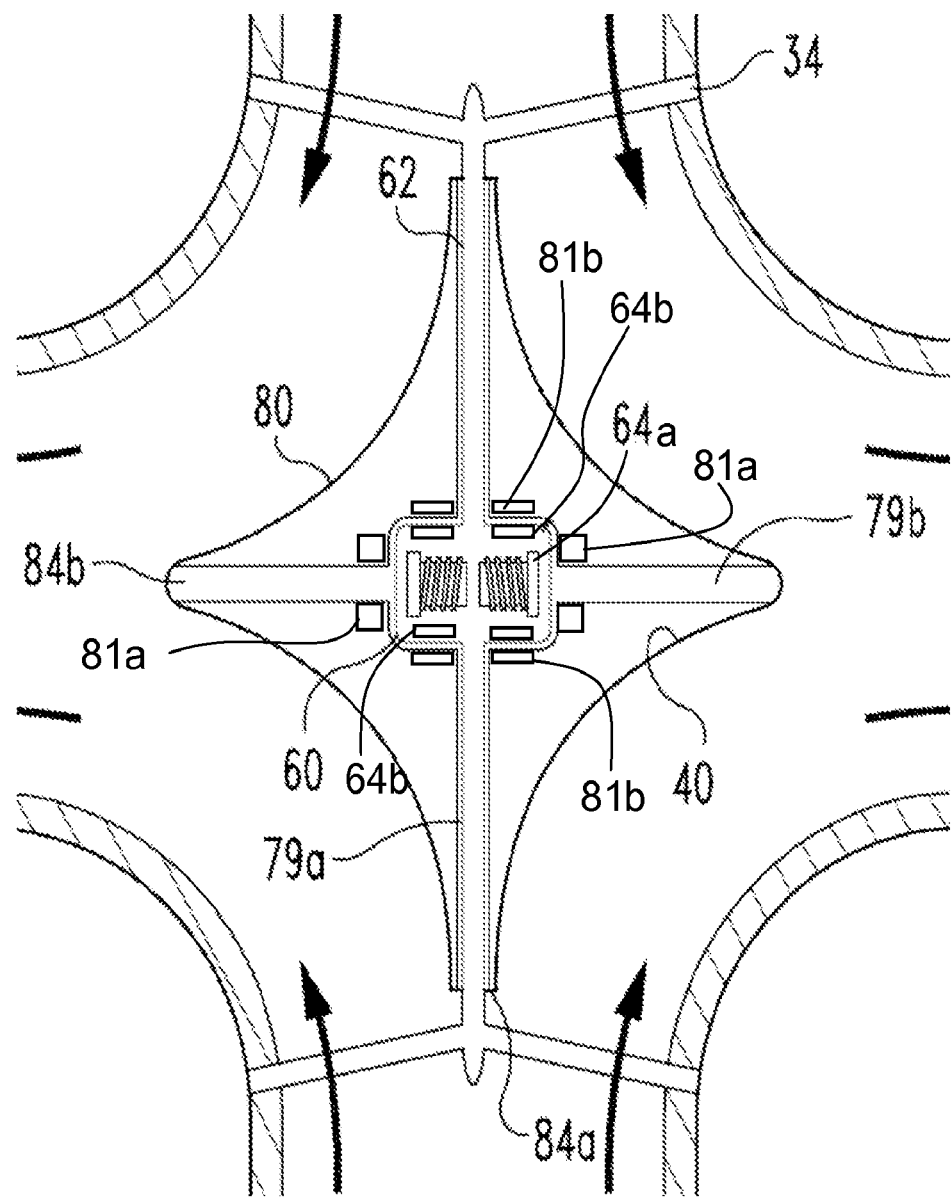
FIG. 2C is an enlargement of a portion of the apparatus of FIG. 2B, showing an alternative bearing arrangement.

Referring to FIG. 2C, it can be seen that some embodiments of the present invention include magnetic relationships between the rotor and the stator intending to provide radial bearing support as well as thrust bearing support. FIG. 2C shows a stator 60 that includes a plurality of permanent magnets 64a adapted and configured for providing torque to rotor 80, as well as a plurality of magnets 64b being adapted and configured to provide a reaction to any net thrust loads of the rotor, and thereby maintain the rotor spinning freely without contact against the stator. Magnets 64b provide repulsive forces relative to an array of magnets 81b mounted within rotor 80. Magnets 81b can be permanent magnets as one example. Magnet 64b can be permanent magnets or electromagnets, as examples. Magnet pairs 64b and 81b coact to repel each other, with pairs on the top of the stator (with respect to the orientation of FIG. 2B) providing a net downward thrust, and magnet pairs 64b and 81b on the bottom of the stator providing a net upward thrust, these net thrusts substantially canceling one another. Preferably, the thrust provided by a top pair or a bottom pair is large enough to overcome any net loading on the rotor, such as by way of the weight of the rotor, net hydraulic thrust forces resulting from pumping, vibratory imbalances, gyroscopic moments as the rotor changes orientation, or the like.

The rotor and stator use radial magnetic bearings of passive design to maintain the relationship between the rotor and stator. The magnetic bearing which levitates the rotor around the shaft includes a plurality of permanent ring magnets and pole pieces arranged along surrounding portions of the rotor and a plurality of permanent disc magnets and pole pieces within the shaft itself. Radially adjacent pairs of these magnets are of like polarity. One part of the magnetic bearing near the central stator core may be used to further maintain the rotor about the rotational axis, and may include a plurality of permanent rod or arcuate magnets disposed in spaced, circular relation around sectors of the stator.

The rotor and stator are axially restrained by magnetic and hydrodynamic forces in combination with mechanical blood-immersed thrust bearings, or touchdowns. A predetermined amount of spacing is included between the touchdowns, so as to allow the rotor/stator assembly to rotate without physical contact. The rotation of the rotor relative to the stator creates a pumping action which results in constant exchange of blood layer between rotor and stator, constantly providing a fresh source of blood. This minimizes the likelihood of clot formation in the gap, and maintains the blood at an acceptable temperature by shortening its residence time in the bearing gap.

Some embodiments of the present invention allow maintenance of a large blood flow gap between impeller and housing. It permits inflow and outflow in multiple directions. In one embodiment, the impeller is axisymmetric with minimal axial thrust force, which aids in reduced stress and balanced operation of the rotor. The use of sealed hollow chambers may reduce the density of the impeller and can be modified to modulate center of mass in the rotor. These chambers reduce gravity induced loads on the thrust bearings, which in turn reduces the likelihood of thrombosis of the blood used to lubricate the bearings.

The inside out arrangement of the rotor and stator components allows the thick magnetic sections to be placed more centrally on the rotor and allows for a narrow flux gap for electrical efficiency. Back-EMF sensing is used to commutate the brushless motor stator, providing attractive and repulsive forces upon the magnetic segments. A control unit and a portable power supply, worn on the user, power the pump drive system. The control unit allows the speed and drive cycle of the motor either to be programmed or interactively determined by the user's activity or condition.

Figure 3:
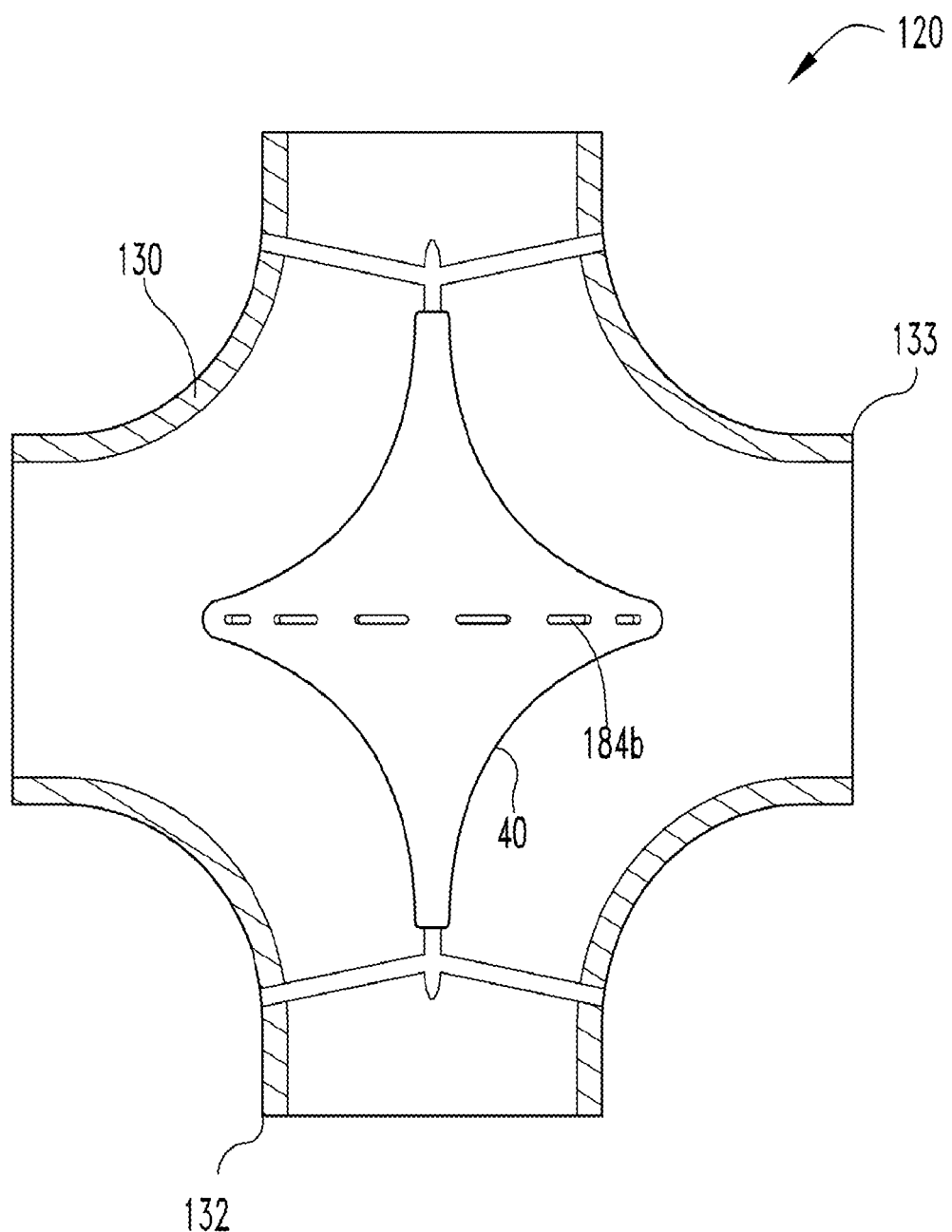
FIG. 3 is a front elevational view in partial cutaway of a pump according to another embodiment of the present invention.

FIGS. 3-6 depict various aspects of a rotary blood pump 120 according to another embodiment of the present invention. A blood pump 120 is shown in FIG. 3, the pump including a housing 130 suspending an impeller assembly 140 by a pair of spiders 134. The impeller 140 is shown having an axisymmetric shape about a rotational axis 141, and further is symmetric about a plane of symmetry 121. A plurality of electrical leads 168 exit housing 130 proximate to one of the legs of a spider 134.

FIG. 3 shows a thin-walled rotor 180 that rotates about a stator 160 which is supported along a centerline 141. Rotor 180 has an outer surface 182 that is adapted and configured to centrifugally pump blood from inlets 132 2 outlets 133.

Preferably, the outer surface 182 has an outer diameter that monotonically increases from either end of the rotor (these ends being supported by spiders 134) toward the middle of rotor 180. In some embodiments, rotor 180 is axisymmetrical about axis 141. In still further embodiments, rotor 181 is further symmetric about a plane 121 that is generally perpendicular to axis 141. With this combination of axisymmetric and planar symmetry rotor 180 encounters no or only negligible net thrust loads along axis 141.

The rotational axis CXLI of pump 120 preferably passes through a pair of opposing inlets 132. The shape of rotor 182 is adapted and configured to viscously induce fluid flow from inlets 132 and to centrifugally provide this same flow at a higher total pressure to at least one outlet 133. At least a portion of the cross-sectional area of outlet 133 is intersected by plane 121.

Figure 4:
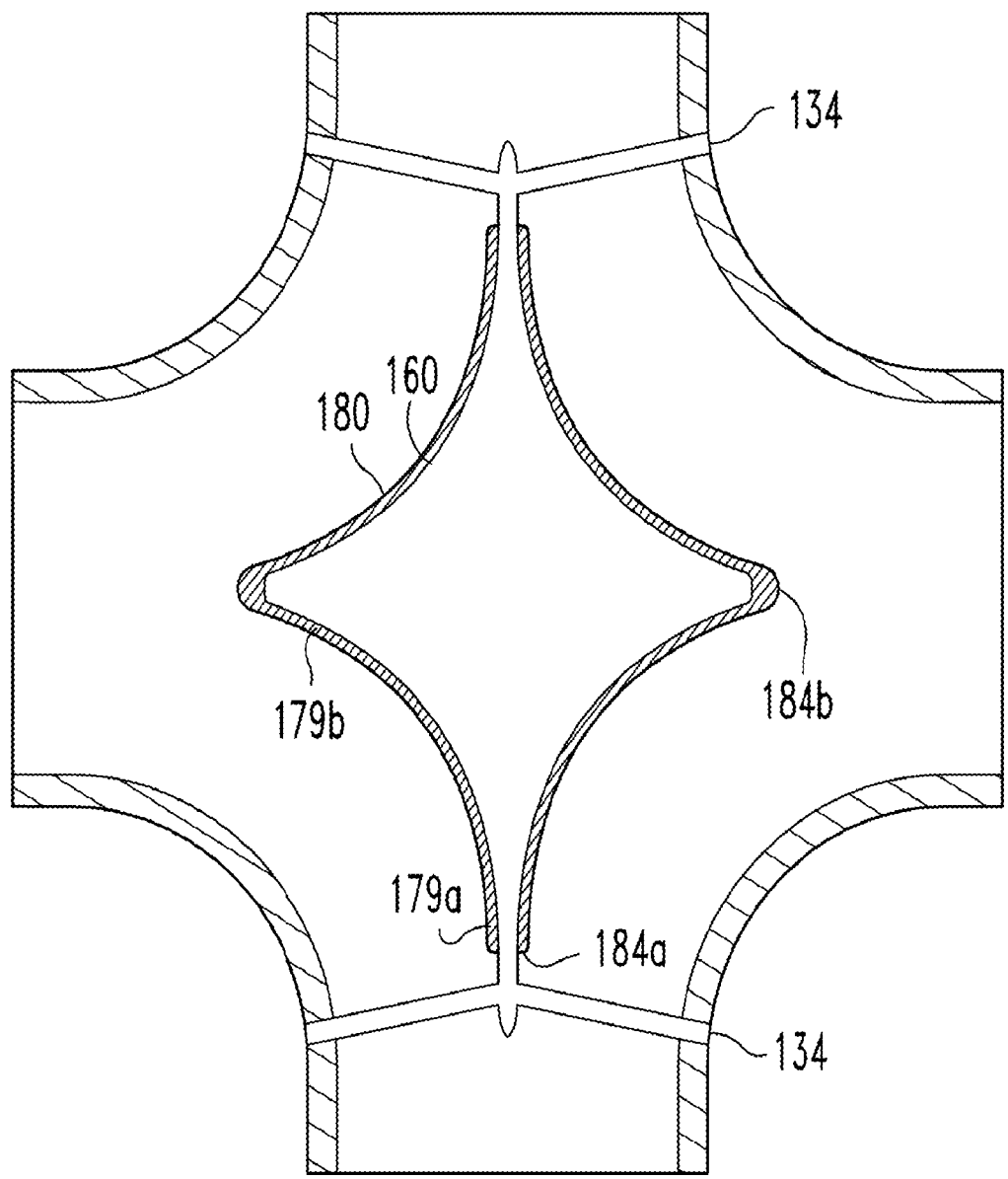
FIG. 4 shows the apparatus of FIG. 3, with additional features being presented in partial cutaway.

FIG. 4 shows a partial cutaway of pump 120. FIG. 4 shows the rotor 180 of impeller 140 in cutaway. Nested within rotor 180, and supported by spiders 134, is an internal stator core 160. A bearing flowpath 179 (shown in crosshatch) is provided in the space between the inner surface of rotor 180 and the outer surface of stator 160. Bearing flowpath 179 includes a feed line that is provided with blood from a pair of annular entrance orifices 184a. Blood flows along the curved path toward an expulsion line 179b, with blood exiting from a plurality of spaced apart exit orifices 184b (also seen in FIG. 3).

As best seen in FIG. 4, the internal surface of rotor 180 and the exterior surface 161 of stator 160 cooperate to define a flow passage 179 there between. Preferably, the external shape of the stator is substantially the same as the internal shape of the rotor, so as to manipulate the various hydraulic forces and provide hydrodynamic suspension of rotor 180 about stator 160. In still further embodiments, the external shape of the stator is substantially the same as the external shape of the rotor, so as to encourage an internal VIP pumping effect similar to the VIP pumping effect provided by the external shape of rotor 180.

The gap between the outer surface of the stator and the inner surface of the rotor is adapted and configured to discourage clotting of the blood. This discouragement can be provided in several ways, including by surface shape, by gap size, by the use of coatings, and the like. It is noted that the flow of blood within the gap is provided without positive displacement of the blood. However, it is further recognized that either the exterior surface of the stator or the internal surface of the rotor can include features that encourage pumping within this flow passage 179. As one example, the internal surface of the rotor can include ridges or valleys either formed or etched into the surface, including ridges or valleys having curvature so as to encourage a central focal action within the flow passage. As another example, the exterior shape of the stator can include ridges or valleys formed or etched into the stator surface so as to discourage localized recirculation.

As best seen in FIGS. 3 and 4, pump 120 includes a plurality of surfaces having shapes consistent with the class of pumps referred to as viscous impelling pumps (VIP). FIG. 3 shows that the outer surface of rotor 180 preferably has such a VIP shape. FIG. 4 shows that the inner surface of rotor 180 as well as the external surface of stator 160 further have such VIP shapes. Further discussion of this shape can be found in U.S. patent application Ser. No. 13/122,797, filed Apr. 6, 2011, incorporated herein with regards to discussion of viscous impelling pumps.

Figure 5:
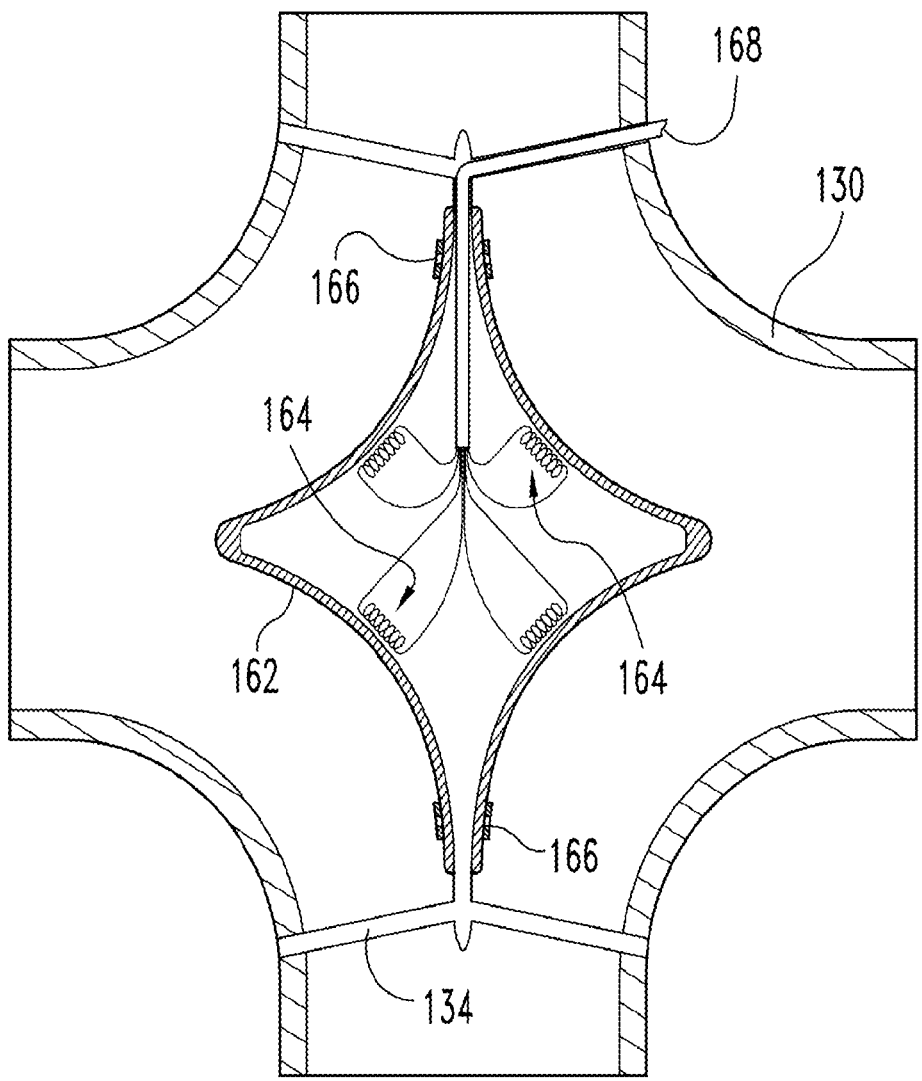
FIG. 5 shows the apparatus of FIG. 3, with additional features being presented in partial cutaway.

FIG. 5 is a cutaway of a portion of the apparatus of FIG. 4. FIG. 5 shows a cutaway of stator 160 supported by spiders 134 within housing 130. The crosshatching of FIG. 5 pertains to the wall thickness of stator 160. It can be seen that stator 160 includes a plurality of internal electrical windings 164 that are provided with electrical power by leads 168 that extend from the core of stator 160 and out of a leg of a spider 134. A source of electrical energy (not shown) provides power by leads 168 to each of the windings 64 in order to induce rotation of rotor 180 (not shown in FIG. 5) about rotational centerline 141. The ends of stator 160 proximate to entrance orifices 184a include a plurality of permanent magnets 166. These permanent magnets 166 can be incorporated on the surface of stator 160, buried within stator 160, or placed within the wall thickness of stator 160. Further, some embodiments include placement of permanent magnets 166 within pockets that are aligned or skewed so as to impart swirl in the fluid passing between the rotor and stator, and to modify cogging torque between the rotor and stator. Magnets 166 provide a magnetic field that uniformly repulses rotor 180, and thereby act as magnetic bearings.

In operation, rotating magnetic fields are induced at each of the windings 164 by the source of electrical power. In some embodiments, this source further receives as an input timing signal the output of a rotational sensor (not shown) that indicates the relative position of rotor 180 relative to stator 160. Still further, in some embodiments, rotor 180 includes a plurality of embedded permanent magnets (not shown), such that the interaction of the field of the embedded permanent magnets and the field created by windings 164 interact so as to rotate rotor 180.

The outer surface of stator 160 and the inner surface of rotor 180 interact to provide a viscous impelling effect that results in the flow of blood inward from annular inlet orifices 184a along rotational axis 141. The relative rotation of stator 180 and stator 160 result in a higher pressure of this induced blood flow in gap 179 proximate to plane 121, such that the plurality of exit orifices 184b release blood from passageway 179 through the exit orifices 184b. This flow of blood within internal passageway 179 provides hydrodynamic bearing-type support of rotor 180 about the body of stator 160. As discussed earlier, further bearing support of rotor 180 is accomplished by magnetic bearings 166 of stator 160. This flow of blood within passageway 179 further acts to provide cooling to stator 160.

Flow orifices 184 have a configuration and a location so as to induce or entrain flow from passage 179 as a result of the low static pressure in the external flow field of rotor 180 proximate to midplane 121. Referring to FIG. 3, it can be seen that the centrifugal action of rotor 180 provides a pumping action with the highest fluid velocity (and therefore lowest static pressure) in the region of the maximum diameter of rotor 180. By careful shaping and placement of apertures 184b this low static pressure can be communicated to the hydrodynamic bearing flow in expulsion line 179b so as to entrain this bearing flow as it nears the apertures.

A second path for the flow of blood is created by the external VIP shape of rotor 180 (as best seen in FIG. 3). As the rotor body 180 rotates about axis 141, blood is induced to flow along the outer surface of rotor 180 from a position proximate to spiders 134 toward the central plane 121. This external flow of blood along the outer surface of rotor body 180 combines with the internal flow from exit orifices 184b, such that impeller 140 provides a combined flow of viscously impelled blood along both internal and external flowpaths.

Figure 6:
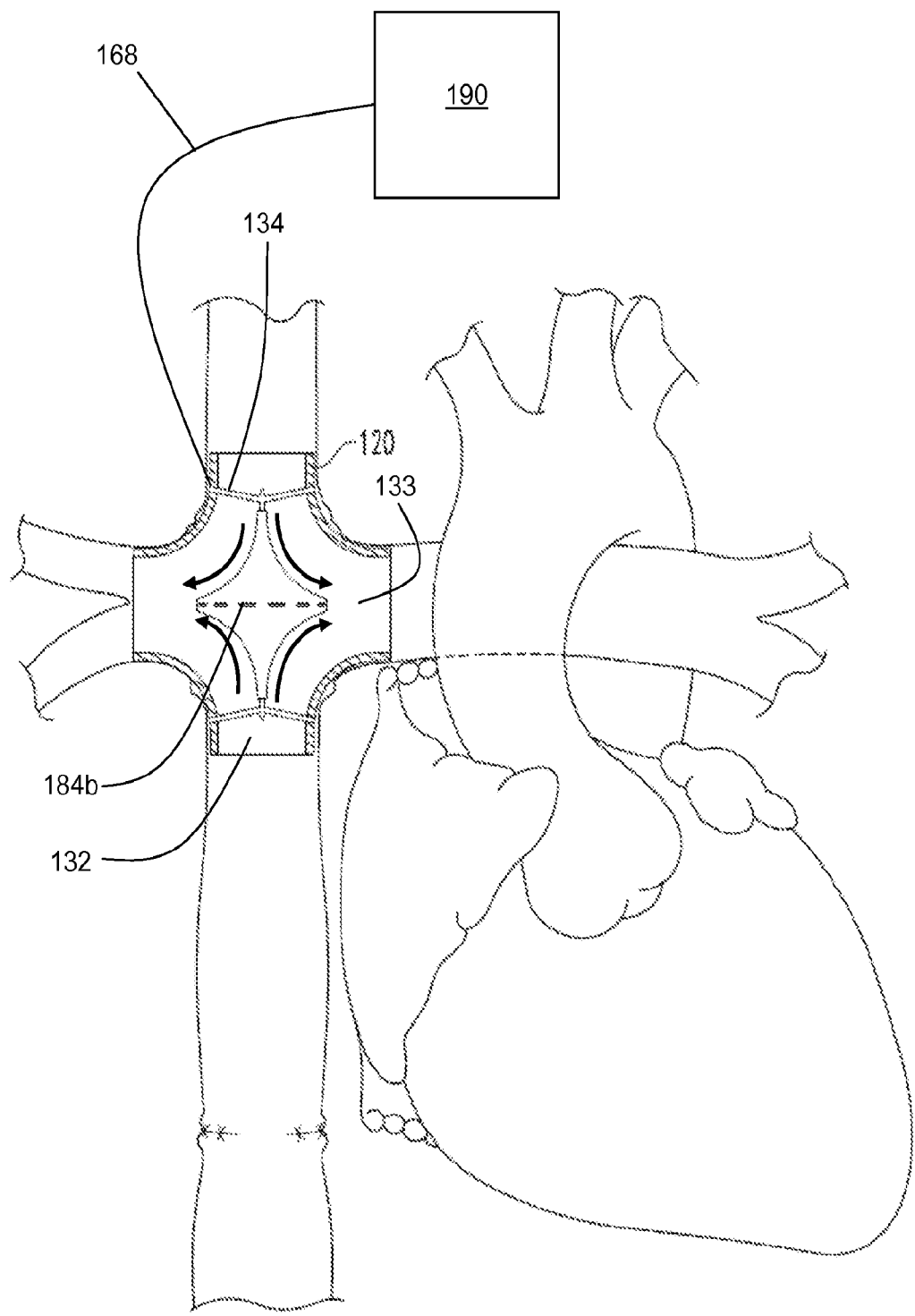
FIG. 6 is a schematic representation of the apparatus of FIG. 3 implanted within a human patient.

FIG. 6 provides a schematic representation of a pump 120 implanted in a patient according to one embodiment of the present invention.

Figure 7:
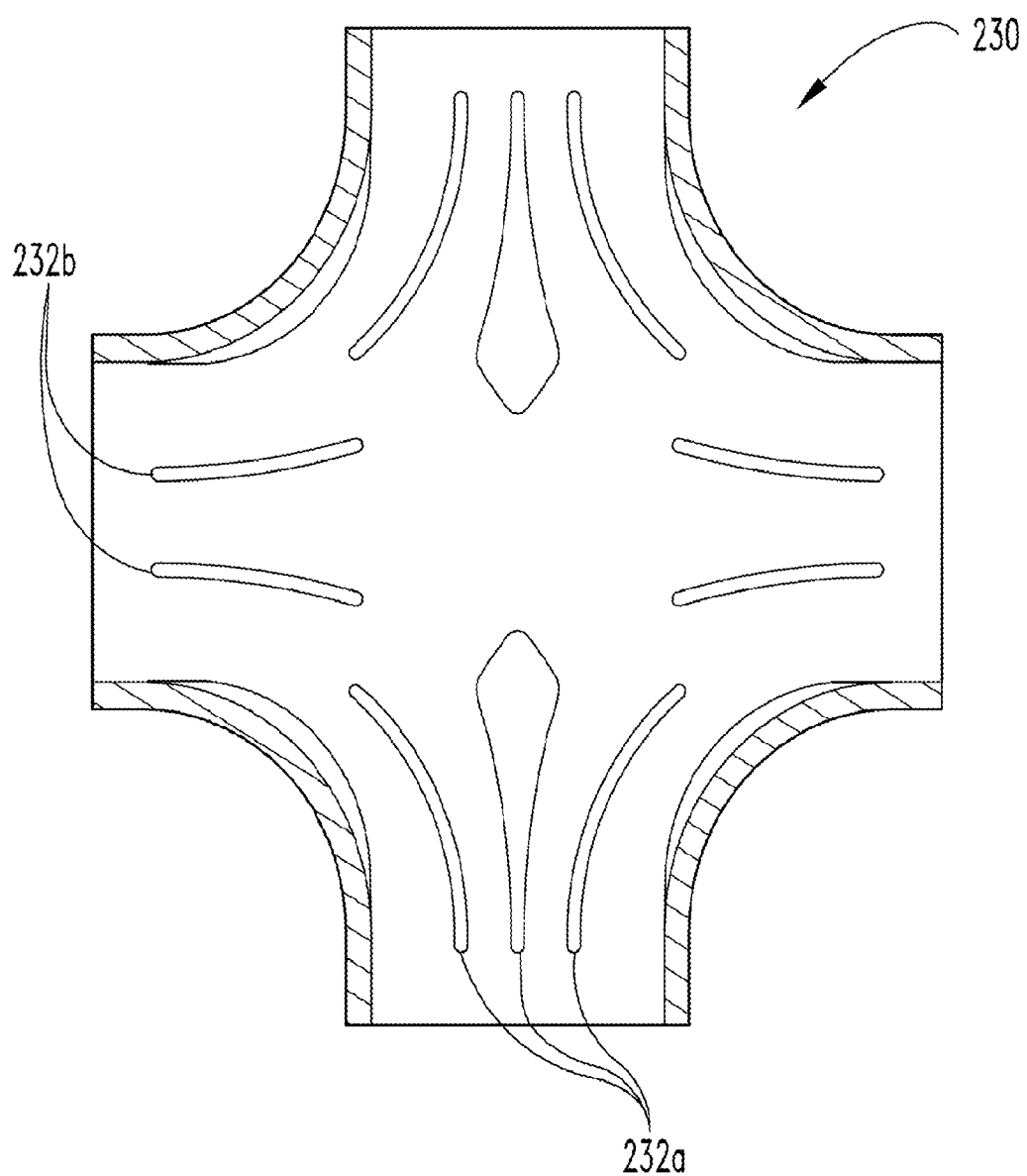
FIG. 7 is a front elevational view in partial cutaway of a housing according to another embodiment of the present invention.

FIG. 7 is a cutaway of a housing 230 according to another embodiment of the present invention. Housing 230 includes a plurality of inlet strakes 232b that are intended to improve the flow characteristics of impeller 140. In some embodiments, flow strakes 232 are projections from the inner surface of housing 230 that are adapted and configured to reduce or eliminate internal volumes with recirculation, and further to reduce the likelihood of blood cells or other materials in the patient's blood being damaged by contact with the implanted pump.

Figure 8:
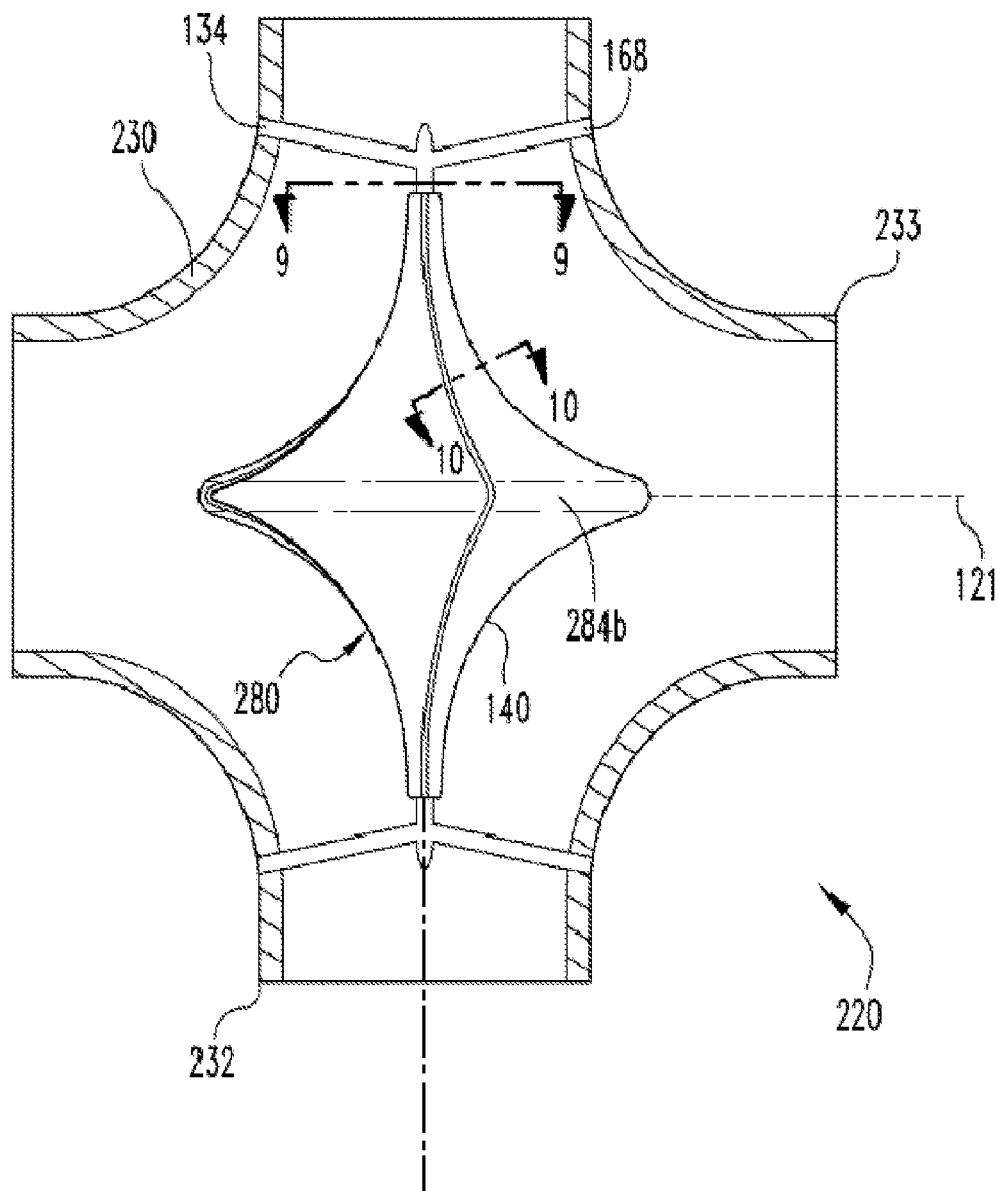
FIG. 8 is a front elevational view in partial cutaway of a pump according to another embodiment of the present invention.
Figure 9:
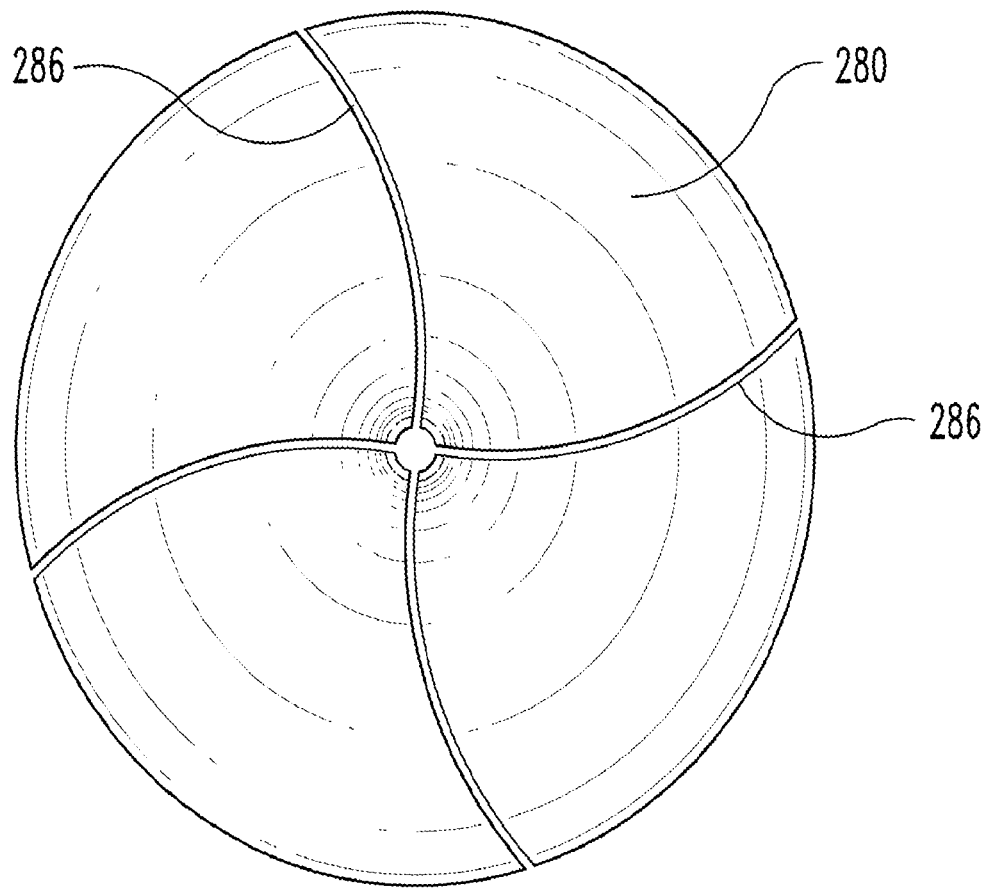
FIG. 9 is a view of the apparatus of FIG. 8 as taken along line 9-9.

FIGS. 8, 9, and 10 depict certain aspects of a pump 220 according to another embodiment of the present invention. Pump 220 includes a rotor 280 having a plurality of bearing flow exit slots 286. Slots 286 extend across at least a portion of the length of rotor 280, and in some embodiments extend along the entire length. These slots 280 are adapted and configured to provide increased flow of blood within bearing path 279, discouragement of blood clotting in the bearing flow path, or improved hydrodynamic suspension of the rotor by decreased sensitivity to clotting.

FIG. 8 shows a flow exit aperture or slot 286 extending along a portion of the surface of rotor 280. The lengthwise shape of the slots can be of any type consistent with the viscous impelling operation of rotor 280. In one embodiment, slots 286 have a curved shape that is generally symmetrical about midplane 221. For purposes of providing balanced internal and external flow, and further with regards to the dynamic balance of the rotor, it is preferable that slots 286 be arranged in a symmetrical pattern about axis 241, as shown in FIG. 9.

Figure 10A:
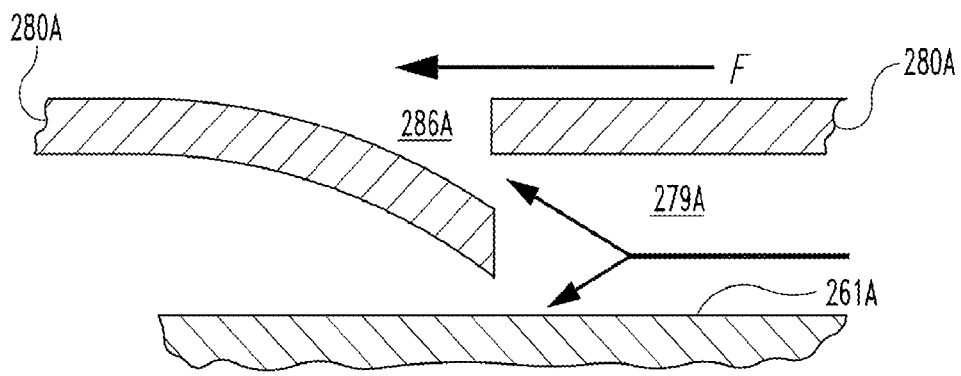
FIG. 10 shows multiple configurations of an exit slot of the apparatus of FIG. 8 as taken along line 10-10: (A) showing a 1st configuration; (B) showing a 2nd configuration; (C) showing a 3rd configuration.

FIG. 10 includes diagrams of three different configurations of exit slots 286, flow path 279, and rotor 280. Each of these three figures is an enlargement of the bearing flow path proximate to the exit slots, and further showing the gap between the outer surface 261 of stator 260 and the inner surface of rotor 280. FIG. 10A shows a first configuration of slot 286a for a rotor 280a that maintains a fixed maximum diameter in the vicinity of the slot. As the noted by arrow F, the flow of fluid over the external surface of rotor 280a is at a relatively fixed diameter for any particular axial location of the slot. The leading edge of the slot is generally flat, but the trailing edge of the slot extends below the surface and into flow path 279a. It can be seen that bearing flow within flow path 279a bifurcates as it encounters the trailing edge.

Figure 10B:
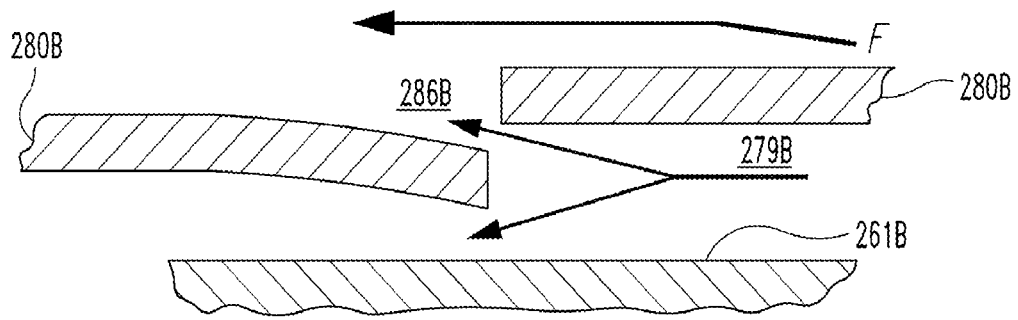
Figure 10C:
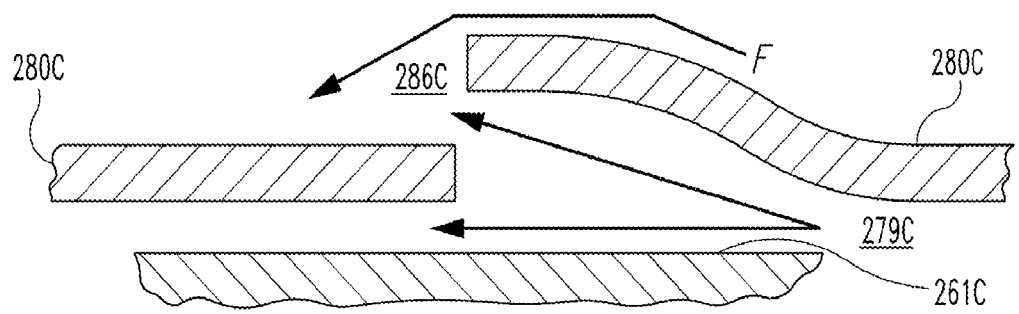

FIG. 10C shows a second configuration in which the leading edge of slot 286c extends radially outward, so as to create a local area of rotor 280c having a maximum diameter greater than the mean maximum diameter. As indicated by arrow F, the externally pumped flow moves, radially outward as it encounters the leading edge of the slot, and then returns to the mean maximum diameter. After passing the slot trailing edge, flow within the bearing flow path 279c can be seen to bifurcate, with a portion of the bearing flow extending radially outward to exit from the slot. FIG. 10B shows a slot configuration 286b that is intermediate of configurations 286a and 286c.

X1. One aspect of the present invention pertains to an apparatus for pumping fluid. The method preferably includes a rotor symmetrical about a rotational axis and having an outer surface adapted and configured for pumping fluid, the rotor interior including a first plurality of permanent magnets. The apparatus preferably includes a stator including a plurality of electrical windings, the windings being located within the interior of the rotor and establishing a radial gap between the magnets and the windings adapted and configured to discourage clotting of the fluid therebetween.

X2. Another aspect of the present invention pertains to an apparatus for pumping fluid. The apparatus preferably includes a symmetrical rotor rotatable about a rotational axis and having an interior and inner and outer surfaces. The apparatus preferably includes a stator located at least in part within the interior of the rotor and supporting the stator. The apparatus preferably includes means for electromagnetically coupling the rotor and the stator. The apparatus preferably includes a housing supporting the stator, the housing including a conductor for providing electrical power to the coupling means, the housing having a pair of opposing inlets, the inlets being generally aligned along the rotational axis, wherein the rotor spins about the stator in response to the application of electrical power to the coupling means.

X3. Another aspect of the present invention pertains to an apparatus for pumping fluid. The apparatus preferably includes a rotor symmetrical about a rotational axis and having an internal shape adapted and configured for centrifugal pumping of fluid and having an interior shape. The apparatus preferably includes a stator having a portion located within the interior shape of the rotor, the portion of the stator having an external shape that cooperates with the interior shape of the rotor to define a flow passage therebetween, wherein rotation of the rotor about the stator results in flow of fluid through the flow passage that may or may not hydrodynamically support rotation of the rotor about the stator.

X4. Another aspect of the present invention pertains to an apparatus for pumping fluid. The apparatus preferably includes a centrifugal rotor having an interior and inner and outer surfaces. The apparatus preferably include a stator having an outer surface, wherein a surface of the stator and a surface of the rotor coact to form a flow passage therebetween, a first supply of fluid flows over another surface of the rotor when the rotor spins about the axis, a second different supply of fluid flows through the flow passage simultaneously with flow of the first supply when the rotor spins about the axis, the rotor being adapted and configured such that the first supply of fluid induces the second supply of fluid.

Yet other embodiments pertain to any of the previous statements X1, X2, X3, or X4 which are combined with one or more of the following other aspects:

Which further comprises a source of electrical power and an electronic controller operably connecting the source to the winding, wherein the rotor spins relative to the stator in response to the controller providing power to the windings Wherein the rotor and the stator electromagnetically coact as a brushless motor.

Wherein the stator and the rotor include a second plurality of permanent magnets for magnetic levitation of the rotor about the stator.

Wherein the rotor and the stator establish a flow path therebetween in which the fluid provides hydrodynamic support of the rotor.

Wherein the rotor includes a thin walled shell.

Wherein the rotor includes opposite ends along the axis and a middle therebetween, and the outer diameter of the rotor increases monotonically from each end toward the middle.

Which further comprises a housing that supports the stator, the housing including two inlets and an outlet, the housing being adapted and configured to be attached to the circulatory system of the animal proximate each of the inlets.

Wherein the outlet is a first outlet and which further comprises a second outlet, the first and second outlets being located to receive fluid flowing within the plane.

Wherein the stator supports the rotor hydrodynamically with fluid.

Wherein the rotor extends between opposing ends along a length, of the axis and which further comprises a pair of magnetic bearings, one bearing being located at one end and the other bearing being located at the other end.

Wherein each the magnetic includes a Halbach array.

Wherein each inlet of the housing includes a strut that locates the stator generally on the axis.

Wherein the motor includes a plurality of permanent magnets attached to the rotor.

Wherein the portion of the stator has an external shape substantially the same as the external shape of the rotor.

Wherein the external shape of the rotor is adapted and configured for centrifugal pumping of fluid.

Which further comprises a plurality of apertures in the rotor, the apertures being adapted and configured to permit the flow of fluid out of the flow passage.

Wherein the stator and the rotor combine to pump fluid from the external shape of the rotor without positive displacement of the fluid.

Wherein the stator and the rotor combine to pump fluid from the flow passage without positive displacement of the fluid.

Wherein the fluid pumped by the external shape of the rotor is first received by the rotor at the same position along the axis as the fluid first received and then pumped from the flow passage.

Wherein the rotor includes a plurality of flow apertures providing fluid communication between the first fluid supply and the second fluid supply.

Wherein the apertures are located proximate to the plane of symmetry.

Wherein flow passage has an entry that is annular in shape.

Wherein the stator is magnetically coupled to the rotor.

Wherein the direction of fluid flowing within the flow passage is toward the plane of symmetry.

Wherein the direction of fluid flowing over the outer surface is toward the plane of symmetry.

Wherein the outer surface of the rotor provides the first supply of fluid by centrifugal operation.

Which further comprises means for electromagnetically coupling the rotor and the stator, the coupling means providing one of more of the following: driving torque to the rotor, thrust support, radial support, vibratory support, or gyroscopic support.

Wherein the stator is supported from a housing by a plurality of struts, and the struts are adapted and configured to limited elastic movement of the rotor and stator relative to the housing.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. An apparatus for pumping blood in the circulatory system of an animal, comprising:
   a rotor symmetrical about a rotational axis and having an external shape adapted and configured for centrifugal pumping of blood, said rotor having an interior shape, said rotor having a plurality of apertures therein;
   a stator having a portion located within the interior shape of said rotor, the portion of said stator having an external shape that cooperates with the interior shape of said rotor to define a flow passage therebetween;
   a housing supporting said stator, said housing having a pair of opposing inlets and an outlet, the inlets being generally aligned along the rotational axis; and
   wherein rotation of said rotor about said stator results in flow of blood through the flow passage, said flow passage being adapted and configured to hydrodynamically support rotation of said rotor about said stator, the apertures of the rotor being adapted and configured to permit the flow of blood out of the flow passage.

2. The apparatus of claim 1 wherein the portion of said stator has an external shape substantially the same as the external shape of said rotor.

3. The apparatus of claim 1 wherein the external shape of said rotor is adapted and configured for centrifugal pumping of blood.

4. The apparatus of claim 1 wherein said stator and said rotor combine to pump blood from the external shape of said rotor without positive displacement of the blood.

5. The apparatus of claim 4 wherein said stator and said rotor combine to pump blood from the flow passage without positive displacement of the blood.

6. The apparatus of claim 5 wherein the blood pumped by the external shape of the rotor is first received by the rotor at the same position along the axis as the blood first received and then pumped from the flow passage.

7. The apparatus of claim 1 wherein the apertures comprise slots.

8. The apparatus of claim 7 wherein the slots are symmetrical about the axis.

9. The apparatus of claim 7 wherein the rotor is symmetrical about a plane perpendicular to the rotational axis, the slots being symmetrical about the plane.

10. The apparatus of claim 9 wherein the slots have a curved shape.

11. The apparatus of claim 1 wherein the stator includes a plurality of permanent magnets configured and adapted to act as magnetic bearings between said rotor and said stator.

12. The apparatus of claim 1 wherein the rotor includes ridges configured and adapted to encourage blood flow within the flow passage.

13. The apparatus of claim 1 wherein the rotor includes valleys configured and adapted to encourage blood flow within the flow passage.

14. The apparatus of claim 1 wherein the stator includes ridges configured and adapted to discourage localized recirculation.

15. The apparatus of claim 1 wherein the stator includes valleys configured and adapted to discourage localized recirculation.

16. The apparatus of claim 1 wherein said stator is supported by a pair of spiders connected to said housing.

17. The apparatus of claim 1 wherein said rotor includes opposing ends and an outer surface, and wherein the diameter of the rotor outer surface monotonically increases from either opposing end toward the middle of the rotor.

18. The apparatus of claim 1 wherein said rotor is axisymmetrical about the rotational axis.

19. The apparatus of claim 18 wherein said rotor is symmetric about a plane perpendicular to the rotational axis.

20. The apparatus of claim 19 wherein the apertures are located in the plane.

21. The apparatus of claim 1 wherein said rotor has two ends along the axis and a midsection therebetween, the apertures being located in the midsection.

22. The apparatus of claim 21 wherein each said inlet including a strut that locates said stator generally on the axis.

23. The apparatus of claim 22 wherein the stator includes a plurality of internal electrical windings configured and adapted to induce rotation of said rotor.

24. An apparatus for pumping blood in the circulatory system of an animal, comprising:
- a rotor symmetrical about a rotational axis and having an external shape adapted and configured for centrifugal pumping of blood, said rotor having an interior shape, said rotor having a plurality of apertures therein;
- a housing having a pair of opposing outlets and a pair of opposing inlets, said housing being adapted and configured to be attached to the circulatory system of an animal proximate to each of the inlets;
- a stator having a portion located within the interior shape of said rotor, the portion of said stator having an external shape that cooperates with the interior shape of said rotor to define a flow passage therebetween, the portion of the stator being symmetric about the rotational axis;
- a central shaft coincident on the rotational axis and having two opposite ends, said shaft supporting said stator, wherein each end of said shaft is supported by a corresponding plurality of struts, each said strut being attached to said housing proximate to an inlet proximate to the shaft end; and
- wherein rotation of said rotor about said stator results in flow of blood through the flow passage, said flow passage being adapted and configured to hydrodynamically support rotation of said rotor about said stator, the apertures of the rotor being adapted and configured to permit the flow of blood out of the flow passage.

25. The apparatus of claim 24 wherein the portion of said stator has an external shape substantially the same as the external shape of said rotor.

26. The apparatus of claim 24 wherein the external shape of said rotor is adapted and configured for centrifugal pumping of blood.

27. The apparatus of claim 24 wherein said stator and said rotor combine to pump blood from the external shape of said rotor without positive displacement of the blood.

28. The apparatus of claim 24 wherein said stator and said rotor combine to pump blood from the flow passage without positive displacement of the blood.

29. The apparatus of claim 28 wherein the blood pumped by the external shape of the rotor is received by the rotor at the same position along the axis as the blood is received and then pumped from the flow passage.

30. The apparatus of claim 24 wherein the apertures are arranged symmetrically about the axis.

31. The apparatus of claim 24 wherein the rotor is symmetrical about a plane perpendicular to the rotational axis.

32. The apparatus of claim 24 wherein the stator includes a plurality of internal electrical windings configured and adapted to induce rotation of said rotor.

33. The apparatus of claim 24 wherein the stator includes a plurality of permanent magnets configured and adapted to act as magnetic bearings between said rotor and said stator.

34. The apparatus of claim 24 wherein the rotor includes ridges configured and adapted to encourage blood flow within the flow passage.

35. The apparatus of claim 24 wherein the rotor includes valleys configured and adapted to encourage blood flow within the flow passage.

36. The apparatus of claim 24 wherein the stator includes ridges configured and adapted to discourage localized recirculation.

37. The apparatus of claim 24 wherein the stator includes valleys configured and adapted to discourage localized recirculation.

38. The apparatus of claim 24 wherein said rotor includes opposing ends and an outer surface, and wherein the diameter of the rotor outer surface monotonically increases from either opposing end toward the middle of the rotor.

39. The apparatus of claim 24 wherein said rotor is axisymmetrical about the rotational axis.

40. The apparatus of claim 24 wherein said rotor has two ends along the axis and a midsection therebetween, the apertures being located in the midsection.

* * * * *